United States Patent [19]

Dabroski

[11] 4,320,750

[45] Mar. 23, 1982

[54] WATER RESISTANT ORTHOPEDIC CAST

[75] Inventor: Winifred C. Dabroski, East Brunswick, N.J.

[73] Assignee: Johnson & Johnson Products, Inc., New Brunswick, N.J.

[21] Appl. No.: 182,544

[22] Filed: Aug. 29, 1980

[51] Int. Cl.³ ............................................. A61F 5/04
[52] U.S. Cl. ................................................. 128/91 R
[58] Field of Search ....................... 128/91 R; 106/111

[56] References Cited

U.S. PATENT DOCUMENTS 3,671,280 6/1972 Smith .................................. 128/91 R
4,136,687 1/1979 Dabroski ........................... 128/91 R

FOREIGN PATENT DOCUMENTS 2736 of 1883 United Kingdom ............. 128/91 R

*Primary Examiner*—Robert W. Michell
*Assistant Examiner*—T. J. Wallen

[57] ABSTRACT

A method of improving the wet-strength characteristics of a plaster of Paris cast is disclosed. The cast bandage is immersed in dip water which contains 2%-15% by weight of a paraffin wax. The wax is dispersed in the dip water by a nonionic or cationic surfactant, and the dip water is maintained at a pH of 7.5 or less. The resulting cast has improved water-resistant properties.

5 Claims, No Drawings

WATER RESISTANT ORTHOPEDIC CAST

BACKGROUND OF THE INVENTION

The use of orthopedic bandages comprising plaster of Paris supported on a flexible material to immobilize the limb of a patient is well known in the art. Plaster of Paris has a known water sensitivity; therefore, patients wearing plaster of Paris casts must take care to avoid the rain and cannot shower. Because of this inconvenience, various improvements in the water resistance of plaster of Paris casts have been made. See, for example, U.S. Pat. Nos. 2,842,120 and 2,842,138 wherein melamine formaldehyde resin precursors have been added to plaster of Paris bandages to improve their water resistance.

Melamine formaldehyde resins have been known to cause allergic responses from the wearers of casts made from bandages of this type. Additionally, it is usually necessary to add the melamine formaldehyde precursors to the bandage in a separate step and, preferably, in an encapsulated form to preclude premature reaction. Various vinyl polymers such as polyvinyl pyrrolidone and polyvinyl acetate have also been added to improve the strength and water resistance of plaster of Paris casts (including the melamine formaldehyde resin-plaster of Paris casts noted above). See U.S. Pat. Nos. 3,671,280 and 3,649,319, respectively. Plaster of Paris casts of this type do show some improved water resistance and strength; however, further improvements in these properties would be desirable. Combinations of polyvinyl acetate and silicones have also been suggested. See U.K. Pat. No. 859,018. The addition of a reactive silicone polymer to improve the water repellency of plaster of Paris casts is disclosed in U.S. Pat. No. 4,136,687.

The addition of a water-repellent or waterproofing agent to a cast bandage presents problems in both the manufacture of the bandage and the application of the bandage to a patient to form the cast. Plaster of Paris is the alphahemihydrate of $CaSO_4$. In the manufacture of the bandage, the plaster of Paris is mixed with a suitable binder such as casein, dextrin or polyvinyl acetate and applied to a gauze or other fabric substrate. The binder adheres the plaster particles on the substrate to prevent dry flake-off and wet slide-off of plaster. Prior to application of the bandage to a patient, a roll of the bandage is dipped into water to activate the plaster. The bandage is allowed to take up water which converts the calcium sulfate hemihydrate to the desired calcium sulfate dihydrate. The conversion to calcium sulfate dihydrate results in hardening of the cast.

The addition of a hydrophobic water-resistant agent to the cast bandage in the bandage manufacturing process interferes with the adhesion of the plaster of Paris particles to the fabric substrate. This can result in increased dry flake or dusting of the particles. The bandage could then have an insufficient plaster content to give the required rigidity to the finished cast.

The addition of a water-repellent material to a plaster of Paris bandage would also normally interfere with the setting of the plaster of Paris. When the plaster is moistened, it absorbs water and sets to a solid rigid mass, calcium sulfate dihydrate. A water-repellent material could be expected to coat individual crystals or particles of the calcium sulfate hemihydrate and prevent water from contacting the crystals, thereby preventing the reaction which results in the formation of the solid calcium sulfate dihydrate. Thus, the process disclosed in U.S. Pat. No. 2,198,776 for manufacturing water-resistant wallboard would not be suitable for manufacturing cast bandages.

SUMMARY OF THE INVENTION

The present invention relates to a method of forming a water-repellent or water-resistant cast by the addition of a water-repellent paraffin wax to the cast bandage immediately prior to the application of the bandage to the patient to form the cast. An emulsion of the paraffin wax is added to the dip water employed to activate the plaster of Paris. The cast bandage picks up a sufficient quantity of the paraffin wax from the dip water to give water-repellent or water-resistant characteristics to the finished cast.

In the method of the present invention, an emulsion of a paraffin wax is added to the dip water used to activate the plaster of Paris of the bandage. The wax emulsion is added to the dip water in sufficient quantity to form a dispersion in the dip water of from 2% to 15% of the wax solids, based on the weight of the dip water. The preferred amount of the wax in the dip water is from 4% to 6%. Increasing the amount of wax in the dip water to more than 15% results in a reduction of the dry-strength characteristics of the finished cast.

The water-repellent material of the present invention is a wax emulsion containing at least 51% of a paraffin wax component having a melting point of at least 100° F., and preferably 130°-160° F., and may contain other materials as a minor component which are compatible with the wax and which have a melting point below the melting point of the major component. Such minor components would include the emulsifying agents, other non-paraffin waxes, aluminum and zirconium salts, and preservatives as hereinafter described. The paraffin waxes are mixtures of straight and branched chain hydrocarbons of high molecular weight containing 23 to 28 carbon atoms.

The paraffin wax composition contains a nonionic or cationic surfactant to maintain the wax as a stable emulsion. An anionic surfactant cannot be used to stabilize the emulsion because such surfactants cause the plaster to precipitate in the dip water.

The commercially available water-repellent wax formulations are aqueous emulsions or dispersions containing from about 20% to 50% wax solids, and from about 6% to 15% of a surfactant system to maintain the wax in the emulsion. The commercially available formulations are diluted with addition water to obtain the wax solids concentration useful in the present invention.

A typical commercial formulation contains approximately 30% by weight of paraffin wax solids; from 4% to 9% by weight of a nonionic surfactant such as a hydrogenated tallow amide ethoxylated with 5 to 10 moles of ethylene oxide; also, from 1% to 3% by weight of a nonionic surfactant such as an ethyoxylated fatty acid such as stearic acid; about 0.1% to 2% by weight of a preservative with the remainder of the formulation being water.

The composition may also contain naturally occuring or microcrystalline waxes in limited amounts as long as the melting point of the mixture is not less than 100° F. Preservatives such as formaldehyde, pentachlorophenol, p-hydroxybenzoates and zirconium salts may be added in small amounts to the wax emulsion.

The pH of the dip water, after the addition of the water-repellant additive, should be from 3 to 7.5. At a pH more than 7.5, there is a possibility that the wax would precipitate from the solution and not be deposited on the cast bandage. It has also been determined that if the pH of the dip water is more than 7.5, the setting time of the finished cast is increased, which is undesirable.

The effectiveness of a water-repellent material added to a cast bandage can be determined by measuring the wet crush strength of a cast. The wet crush strength of a cast system is determined by forming a cast on a two inch diameter dowel; allowing the cast to set; removing the dowel; aging the cast for a period of time, e.g., one to seven days; soaking the cast in water at 72° F. for two minutes; and, then crushing the cast on a Dillon Universal Tester. Another indication of the effectiveness of the water-repellant material is the determination of the amount of water taken up or retained by the cast after soaking the cast in water. This is determined by weighing the cast before and after soaking and is expressed as a percentage increase in the weight of the cast. The difference in the weight of the cast is attributed to the water that is retained by the cast after soaking.

The bead time, that is the length of time that a drop of water applied to the cast will be completely absorbed by the cast, is another test that may be used to determine relative water repellency.

In the examples, the setting time is determined by the following procedure. The cast bandage is dipped in water for five seconds. A cast is formed with five layers of the bandage. A No. 4 needle having a fixed weight of 300 grams is allowed to penetrate the cast. This is repeated every 15 seconds until the needle does not penetrate the cast. The elapsed time until the needle does not penetrate is considered to be the cast setting time.

In addition to improving the water repellency of the cast, the use of the wax emulsion of the present invention also reduces the plaster that is lost from the cast bandages when the bandages are immersed in the dip water. It is advantageous to minimize the amount of plaster lost during the cast dipping, as a high plaster content is necessary to give the desired rigidity to the finished cast.

EXAMPLE 1

A series of dip water solutions were prepared employing commercially available paraffin wax emulsions. The emulsions were added to water in an amount to yield a solution containing 5% solids. Each of the emulsions contained a paraffin wax as a major component and a microcrystalline wax, a surfactant or a stabilizer as a minor component. A four inch wide, five yard long plaster of Paris bandage was immersed in each dip water solution for ten seconds, squeezed to expel excess water and wrapped around a two inch diameter dowel. The casts were removed from the dowel after setting and dried for seven days. A bead time determination was taken. The casts were then immersed in water for two minutes and the wet crush strength determined. A sample which was dipped in tap water without an added wax emulsion served as a control. The results are shown in Table I.

TABLE I

| M.P. of Paraffin Wax Component °F. | M.P. °F. and Type of Minor Component | Bead Time Secs. | Wet Crush Lbs. |
|---|---|---|---|
| 133 | 95 Self Emulsifying Wax | 600+ | 896 |
| 136 | 98.6,111 Saponified Fatty Acids | 600+ | 780 |
| 152.5 | 113 Saponified Ester-Zirconium Salt | 239 | 711 |
| 131 | 95 Zirconium Salt | 145 | 613 |
| 125.5 | 97 | 444 | 830 |
| 143.5 | 113 Saponified Fatty Acid | 546 | 845 |
| 143.5 | 113 Aluminum Salt | 600+ | 776 |
| Control | No Wax | 11 | 400 |

EXAMPLE II

In the next series of experiments, emulsions were evaluated in the following manner:

A dip solution was prepared by diluting a commercial emulsion to 2.5% to 6% solids. A 4 inch×5 yard bandage was immersed in the dip solution for five seconds, squeezed and wrapped around a two inch diameter dowel. The casts were set, removed from the dowel and after seven days drying, wet crush strength was measured after a 2 minute water immersion.

The results are shown in Table II in order of the wet crush strengths obtained.

TABLE II

| Trade-name | Made By | Type | Strength | In Dip Water Wet Crush | Bead |
|---|---|---|---|---|---|
| Jer-Dri | Jersey | Paraffin Waxes | 6% | 831 | 315 |
| RTL | State |  | 5% | 898 | 600+ |
|  |  |  | 2½% | 840 | 318 |
| Nalan-W | Du Pont | Paraffin Wax Mixtures | 5% | 755 | 600+ |
|  |  |  | 2½% | 688 | 191 |
| Nalan GN | Du Pont | Paraffin Wax & Polymer | 5% | 680 | 600+ |

EXAMPLE III

A 26% solids wax emulsion, available as Warel C-S from Reliance Chemical Products Company, with a wax melting point of 136° F., emulsified with saponified fatty acids, having a pH of 4.5–4.9, and containing 6–8% of aluminum and zirconium salts was diluted with water to make solutions containing the % solids cited in the table below. A 4 inch×5 yard bandage dipped in this solution for five seconds, wrapped in the usual manner, after drying for seven days had the following properties:

| Solids % | Dry Crush lbs. | Wet Crush lbs. | Bead Time secs. | Water Absorption % |
|---|---|---|---|---|
| 12 | 620 | 633 | 600+ | 0.7 |
| 6 | 805 | 833 | 600+ | 1.4 |
| 5 | 913 | 784 | 555 | 2.1 |
| 4 | 999 | 708 | 304 | 5.1 |
| 3 | 937 | 750 | 207 | 4.7 |
| 1.5 | 893 | 616 | 77 | 7.4 |
| 0 | 935 | 400 | 9 | 17.6 |

EXAMPLE IV

A 25% solids wax emulsion available as Aquarol LM from Arkansas Company, Inc., with a wax melting point of 143.5° F., emulsified with a cationic emulsifier, a pH of 4.2 and containing about 5% of a metallic salt was diluted with water to make solutions of % solids in the table below. A 4 inch×5 yard bandage dipped in this solution for five seconds, wrapped in the usual manner, after drying for seven days had the following properties:

| Solids % | Dry Crush lbs. | Wet Crush lbs. | Bead Time secs. | Water Absorption % |
|---|---|---|---|---|
| 8 | 678 | 700 | 558 | 1.3 |
| 5 | 893 | 816 | 552 | 1.0 |
| 4 | — | 779 | 531 | 1.6 |
| 3 | 947 | 865 | 481 | 1.7 |
| 1.5 | 997 | 683 | 62 | 5.8 |
| 0.7 | 900 | 388 | 13 | 15.4 |
| 0 | 935 | 400 | 9 | 20.8 |

EXAMPLE V

A 20% solids emulsion, available as Zonyl NWJ from Du Pont, comprising about 15% paraffin wax of melting point 143.5° F. and 5% of an acrylate ester type fluorocarbon, emulsified with a cationic surfactant and a pH of 4.0 was diluted with water to make the % solids concentrations cited below. A 4 inch×5 yard bandage dipped into this solution, wrapped in the usual manner, after drying for seven days had the following properties:

| Solids % | Dry Crush lbs. | Wet Crush lbs. | Water Absorption % |
|---|---|---|---|
| 15 | 753 | 630 | — |
| 10 |  | 745 | 2.1 |
| 7.5 | 863 | 812 | — |
| 5 |  | 815 | 3.2 |
| 3.75 | 960 | 740 | 4.4 |
| 2.5 |  | 730 | 4.4 |
| 2 | 895 | 672 | 5.5 |
| 1.4 | 950 | 587 | — |
| 1.25 |  | 505 | 12.4 |
| 0 | 935 | 473 | 19.5 |

EXAMPLE VI

A 25% wax emulsion, with a wax melting point of 143.5° F., emulsified with saponified fatty acids emulsifier, a pH of 4.8 and containing 6%–8% of zirconium acetate was diluted with water to the appropriate concentrations. A 4 inch×5 yard bandage dipped into the solution, wrapped in the usual manner, after drying for seven days had the following properties:

| Solids % | Dry Crush lbs. | Wet Crush lbs. | Bead Time secs. | Water Absorption % |
|---|---|---|---|---|
| 12 | 963 | 650 | 488 | 2.8 |
| 6.1 | 959 | 865 | 493 | 2.1 |
| 5.0 | 926 | 859 | 464 | 1.7 |
| 4.0 | 988 | 696 | 176 | 5.6 |
| 1.5 | 910 | 523 | 25 | 10.9 |
| 0 | 935 | 400 | 9 | 20.7 |

EXAMPLE VII

A 50% solids emulsion, available as Jer-Dri RTL from Jersey State Chemical Company, comprising a major amount of a paraffin wax of melting point 133° F. and a minor amount of a modified petroleum wax of melting point 130° F., made with a nonionic emulsifier and having a pH of 8.5 to 9.5 was diluted with water to the appropriate concentrations. A 4 inch×5 yard bandage dipped into the solution for five seconds, wrapped in the normal manner, had after drying for seven days, the following properties:

| Solids % | Dry Crush lbs. | Wet Crush lbs. | Bead Time secs. | Water Absorption % |
|---|---|---|---|---|
| 15.0 | 946 | 966 | 600+ | 0.9 |
| 10.0 | 975 | 953 | 600+ | 0.9 |
| 7.5 | 940 | 894 | 588 | 0.8 |
| 5 | 948 | 842 | 519 | 1.9 |
| 4.2 | 922 | 815 | 392 | — |
| 4 | 923 | 844 | 338 | 1.8 |
| 2.5 | 950 | 675 | 170 | 6.7 |
| 0 | 896 | 373 | 8 | 17.6 |

EXAMPLE VIII

This example shows the effect of the pH of the dip water on the setting time of the bandages. The paraffin wax of Example III was added to dip water at a 5% concentration. The pH of the dip was varied and the setting times of a cast made from bandages immersed into the dip water was determined. The results were:

| pH | Setting Time Minutes:Seconds |
|---|---|
| 3.1 | 5.10 |
| 6.6 | 7.30 |
| 7.5 | — |
| 7.8 | 12.30 |
| 8.5 | 15.00 |
| 9.5 | 15.00 |
| 10.0 | 15.00 |

EXAMPLE IX

A series of cast bandages was dipped into water and into water containing a paraffin wax. The percent plaster loss of the bandages was determined by weighing the plaster that was removed from the bandage during the dipping process and comparing that to the weight of the dry bandage. The results are shown in the following table:

|  | % Plaster Loss |
|---|---|
| Water Control | 4.6 |
| 5% Paraffin Wax of Example VII | 3.7 |
| 2% Paraffin Wax of Example V | 3.5 |
| 5% Paraffin Wax of Example III | 2.4 |

The plaster loss was reduced when the dip water contained a paraffin wax.

I claim:

1. A method of forming a water-resistant orthopedic cast comprising immersing a plaster of Paris cast bandage into water containing a dispersion of from 2% to 15% by weight of wax solids, at least 51% of said wax solids being paraffin waxes having a melting point between 100° F. and 160° F., said wax solids being dispersed in said water with a cationic or nonionic surfactant; removing the cast bandage from the aqueous dispersion and applying the bandage to form a cast.

2. The method of claim 1 in which the dispersion contains from 2%-6% by weight of the paraffin wax solids.

3. The method of claim 1 in which the dip water is maintained at a pH of from 3 to 7.5.

4. The method of claim 1 in which the wax solids consist of paraffin waxes.

5. The method of claim 1 in which the wax solids include microcrystalline waxes.

* * * * *

UNITED STATES PATENT AND TRADEMARK OFFICE
Certificate

Patent No. 4,320,750                                                Patented March 23, 1982

Winifred Christina Dabroski

Application having been made by Winifred Christina Dabroski, the inventor named in the patent above-identified, and Johnson and Johnson Products, Inc., the assignee, for the issuance of a certificate under the provisions of Title 35, Section 256, of the United States Code, adding the names of Julius Alfred Lindquist and George Julius Lukacs as joint inventors, and a showing and proof of facts satisfying the requirements of the said section having been submitted, it is this 21st day of Feb., 1984, certified that the name of the said Julius Alfred Linquist and George Julius Lukacs are hereby added to the said patent as joint inventors with the said Winifred Christina Dabroski.

Fred W. Sherling,
*Associate Solicitor.*